(12) United States Patent  
Swenson

(10) Patent No.: US 11,600,369 B2  
(45) Date of Patent: *Mar. 7, 2023

(54) PHARMACY PREDICTIVE ANALYTICS

(71) Applicant: CareFusion 303, Inc., San Diego, CA (US)

(72) Inventor: David D. Swenson, Encinitas, CA (US)

(73) Assignee: CAREFUSION 303, INC., San Diego, CA (US)

( * ) Notice: Subject to any disclaimer, the term of this patent is extended or adjusted under 35 U.S.C. 154(b) by 153 days.

This patent is subject to a terminal disclaimer.

(21) Appl. No.: 17/125,857

(22) Filed: Dec. 17, 2020

(65) Prior Publication Data

US 2021/0134422 A1    May 6, 2021

Related U.S. Application Data

(63) Continuation of application No. 15/891,809, filed on Feb. 8, 2018, now Pat. No. 10,872,687.

(51) Int. Cl.
*G16H 20/13* (2018.01)
*G16H 50/20* (2018.01)
(Continued)

(52) U.S. Cl.
CPC ............. *G16H 20/13* (2018.01); *G06Q 50/22* (2013.01); *G07F 17/0092* (2013.01);
(Continued)

(58) Field of Classification Search
CPC ........ G16H 20/13; G16H 40/20; G16H 50/20; G16H 20/10; G06Q 50/22; G07F 17/0092
See application file for complete search history.

(56) References Cited

U.S. PATENT DOCUMENTS 9,150,119 B2 * 10/2015 Henderson ............. B60M 1/346
9,864,842 B2 *  1/2018 Hyde ..................... G06Q 10/10
(Continued)

FOREIGN PATENT DOCUMENTS

CN          105074765 A       11/2015
CN          105408933 A        3/2016
(Continued)

OTHER PUBLICATIONS

Chinese Office Action for Application No. 201980012262.0, dated Aug. 24, 2021, 11 pages including translation.
(Continued)

*Primary Examiner* — Evangeline Barr  
*Assistant Examiner* — Jordan L Jackson  
(74) *Attorney, Agent, or Firm* — Morgan, Lewis & Bockius LLP

(57) ABSTRACT

A system, including a memory storing instructions and a processor configured to execute the instructions is provided. The instructions executed by the processor cause the system to retrieve a diagnostic information for a patient, to retrieve a physician information for a physician in charge of the
(Continued)

patient, and to determine an anticipated medication prescription for the patient based on the diagnostic information, the physician information, and a medication prescribing pattern stored in the memory. A method for using the system and a non-transitory, computer readable medium including the instructions are also provided.

20 Claims, 5 Drawing Sheets

(51) Int. Cl.
    *G16H 20/10*     (2018.01)
    *G16H 40/20*     (2018.01)
    *G06Q 50/22*     (2018.01)
    *G07F 17/00*     (2006.01)

(52) U.S. Cl.
    CPC ............ *G16H 20/10* (2018.01); *G16H 40/20* (2018.01); *G16H 50/20* (2018.01)

(56) References Cited

U.S. PATENT DOCUMENTS

| | | | |
|---|---|---|---|
| 2002/0143579 A1 | 10/2002 | Docherty et al. | |
| 2005/0197862 A1 | 9/2005 | Paterson et al. | |
| 2010/0161353 A1* | 6/2010 | Mayaud | G16H 10/60 |
| | | | 707/752 |
| 2014/0262690 A1 | 9/2014 | Henderson et al. | |
| 2017/0109480 A1 | 4/2017 | Vahlberg | |
| 2017/0357760 A1 | 12/2017 | Han et al. | |
| 2018/0082042 A1 | 3/2018 | Volyanskyy et al. | |

FOREIGN PATENT DOCUMENTS

| | | | | |
|---|---|---|---|---|
| CN | 107533582 A | | 1/2018 | |
| JP | 2008210414 A | * | 9/2008 | ............ G06Q 10/06 |

OTHER PUBLICATIONS

Eryu Xia et al., Learning Doctors' Medicine Pattern for Chronic Disease Treatment by Mining Electronic Health Records: A Multi-Task Learning Approach, AMIA Annu Symp Proc. 2017 1828-1837 (Dec. 31, 2016) available at https://europepmc.org/article/PMC/5977645 (Year: 2016).

International Preliminary Report on Patentability from the International Preliminary Examining Authority for Application No. PCT/US2019/017018, dated May 4, 2020, 20 pages.

International Search Report and Written Opinion for Application No. PCT/US2019/017018, dated May 7, 2019, 9 pages.

International Written Opinion from the International Preliminary Examining Authority for Application No. PCT/US2019/017018, dated Jan. 23, 2020, 7 pages.

S. Byrne et al., Using Neural Nets for Decision Support in Prescription and Outcome Prediction in Anticoagulation Drug Therapy, 5th Int. Workshop on Intelligent Data Analysis in Medicine and Pharmacology 9-12 (Aug. 2000) (Year: 2000).

\* cited by examiner

PHARMACY PREDICTIVE ANALYTICS

CROSS REFERENCE TO RELATED APPLICATIONS

This application is a continuation application of U.S. application Ser. No. 15/891,809, entitled "PHARMACY PREDICTIVE ANALYTICS," filed on Feb. 8, 2018, now U.S. Pat. No. 10,872,687, the entirety of which is incorporated herein by reference.

BACKGROUND

The present disclosure is generally related to medication management in healthcare facilities. More specifically, the present disclosure relates to predicting medication requests for patients to shorten the time and cost for medication dispensing and optimizing storage efficiency.

Current medication storage systems are required to keep a large variety of medications on hand to treat a wide variety of potential medical diagnosis. Immediate medication availability optimizes patient treatment and prevents many diseases from progressing. For this reason, hospitals often employ patient care area based cabinets which can provide immediate availability to stocked medications. Medications not stocked in the care area based cabinets require delivery from pharmacy in response to a physician order which can take time and delay treatment. In the patient care area storage scenario, and because physician prescribing patterns change over time, it is important for pharmacy to periodically review the medication inventory to assure medications stored in the cabinets are the most commonly prescribed medication types. Prescription of a medication not in the patient care area cabinet can result in treatment delays and typically is more expensive to deliver from pharmacy. Further, when medications go un-prescribed and remain in cabinets for extended periods, a portion of the medications may exceed their shelf life and be discarded.

SUMMARY

In a first embodiment, a system including a memory storing instructions and a processor configured to execute the instructions is provided. The instructions executed by the processor cause the system to retrieve a diagnostic information for a patient, to retrieve a physician information for a physician in charge of the patient, and to determine an anticipated medication based on the diagnostic information, the physician information, and a medication prescribing pattern stored in the memory. This determination can allow a pharmacy to anticipate the need for a medication and send it to the patient proactively, precluding delays in medication administration treatment.

In a second embodiment, a computer-implemented method includes retrieving a personal information from a patient upon admission of the patient to a healthcare facility, wherein the personal information includes a symptom. The computer-implemented method includes retrieving a diagnostic based on the symptom and determining an anticipated medication prescription for the patient based on the personal information for the patient, on the diagnostic, and on a medication prescribing pattern stored in a memory. The computer-implemented method also includes prompting a delivery and storing of a first dose and subsequent supply of a medication from the anticipated medication prescription in an automated dispensing machine.

In further embodiments, a non-transitory, computer readable medium comprising instructions which, when executed by a processor in a computer cause the computer to perform a method. The method includes retrieving a personal information from a patient upon admission of the patient to a healthcare facility, wherein the personal information includes a symptom, retrieving a diagnostic based on the symptom, and determining a predicted medication prescription for the patient based on the personal information for the patient, on the diagnostic, and on a medication prescribing pattern stored in a memory. The method further includes prompting a delivery and storing of a first dose and subsequent supply of a medication from the anticipated medication prescription in an automated dispensing machine.

BRIEF DESCRIPTION OF THE DRAWINGS

In the figures, elements having the same or similar reference numeral have the same or similar functionality or configuration, unless expressly stated otherwise.

DETAILED DESCRIPTION

Figure 1:
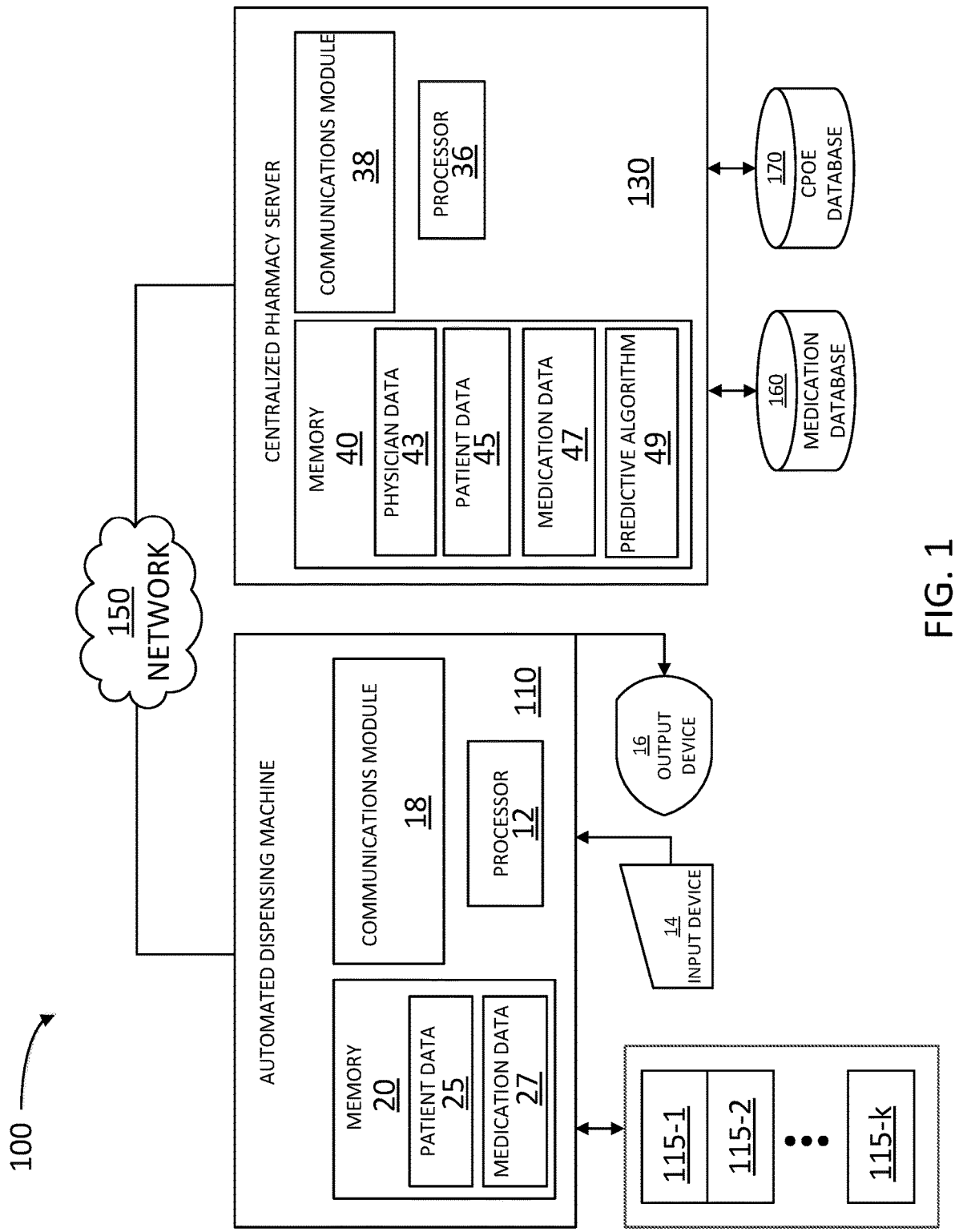
FIG. 1 illustrates a system for medication management, according to some embodiments.

The present disclosure is directed to medication delivery systems using predictive analytics to shorten a time lapse between a patient admission to an acute healthcare facility and an effective delivery of an appropriate medication to the patient. In some embodiments, a medication storage system is configured to store medications that have a high likelihood of being delivered to the appropriate patient in a short period of time, even during an emergency situation. For example, storage systems as disclosed herein are configured to store medications in a selected automated dispensing machine most likely to be used by a patient in the proximity of the selected automated dispensing machine.

In conventional systems, pharmacy management (e.g., storage and delivery of medications) includes reactive tasks. Typical steps in medication management involve a physician writing a prescription (e.g., in written form) based on examination and diagnosis of a patient. In some configurations, physicians may enter prescription requests through a computerized system (e.g., a centralized pharmacy server). Based on the prescription request, a pharmacist reviews the prescription order for safety and appropriateness, and then prepares and dispenses the medication. Embodiments disclosed herein include analytical methods and steps that afford pharmacists the opportunity to predictively position medications in advance of the physician prescription. For example, in some embodiments a centralized pharmacy server may use a patient diagnosis, patient demographic and other medication information collected at the time of patient admission, to predictively assure that medications highly likely to be prescribed by a physician are positioned close to the patient's location, prior to the physician ordering them. Some embodiments include a standardized formulary for improved medication management in which similar patient conditions, symptoms and diagnosis lead to similar medication prescriptions. Accordingly, some embodiments include methods and steps wherein a physician preference for prescribing one medication or another decreases in weight to predict a medication prescription, relative to a cumulative history of medication prescription aggregated over multiple physicians, multiple patients, and multiple healthcare facilities. In some embodiments, a medication prescription may be determined prior to the physician making a prescription, thereby saving time and providing a more reliable process with repeatable and verifiable outcomes. Further, cabinet set up and optimization approaches in embodiments as disclosed herein include disposing and replacing residual medications from cabinets and automated dispensing machines. For example, medications that are seldom prescribed and already present in the cabinet can be replaced with other medications that are more likely to be dispensed to a patient, according to certain diagnosis and treatment plan.

In current medication management systems, such as the "all medications model" described below, it has been found that about 20% or even more of medications stored in cabinets and delivery systems are not prescribed or accessed, for about six (6) months, or even more. These unused medications often take the place of new commonly prescribed medications which must be sent from a central pharmacy areas, causing treatment delays. Accordingly, hospitals using an "all medications" model, which typically includes stocking 90-95% of the typical prescribing needs in storage cabinets throughout a nursing unit, may include up to 20% of stored medications that are not typically prescribed by the physicians practicing in that area. In some situations, perhaps even a large portion of the stored medications (from a few percent to maybe 10% or even more) may in fact expire before administration to a patient. Thus, storage costs, medications costs, and overhead control of medication delivery are burdened by this excess storage capability. Furthermore, storage inefficiency impacts the quality of patient care, especially when a desired medication is not immediately available to a patient when in urgent need. For example, in some circumstances it is found that it is three (3) times more expensive to retrieve a medication when the medication is not available in a cabinet or automated dispensing unit close to a patient, as compared to a situation where it is. Further, it has been found that the time to deliver the first dose for medications retrieved remotely rather than in a cabinet located near the patient, or in the patient room, is approximately forty (40) minutes longer or more, on average.

Some of the advantages of embodiments consistent with the present disclosure include predicting a medication that may be prescribed to a patient by a physician at the time of diagnostic, or even earlier, after patient admission to the healthcare facility. Thus a medication request to an automated dispensing machine or cabinet may have a quick, positive response. Accordingly, little time is wasted in waiting for the appropriate medication to reach the nurse or healthcare personnel in charge of delivery to the patient. In some embodiments, a machine learning algorithm ensures that as soon as a patient has been admitted with certain symptoms and/or medical history, the desired medications will be available to the nurse or healthcare personnel responsible for the patient when desired.

FIG. 1 illustrates a system 100 for medication management (e.g., medication storage and delivery), according to some embodiments. System 100 includes an automated dispensing machine 110 having a memory 20, a processor 12, and a communications module 18. Memory 20 includes patient data 25 and medication data 27. Patient data 25 may include information associated with patients that receive medications from automated dispensing machine 110. Medication data 27 contains an updated inventory of medications stored in automated dispensing machine 110. Automated dispensing machine 110 also includes an input device 14 (e.g., a mouse, a keyboard, a touch screen display, and the like) and an output device 16 (e.g., a display, a speaker, and the like). Accordingly, a user of automated dispensing machine 110 may enter commands and queries to automated dispensing machine 110 with input device 14, and receive graphic and other information from automated dispensing machine 110 with output device 16. In some embodiments, automated dispensing machine 110 includes one or more storage drawers 115-1, 115-2, through 115-$k$ (hereinafter, collectively referred to as storage drawers 115), where 'k' may be any integer value. Storage drawers 115 may include containers having medications to be prescribed and administered to patients, wherein the containers may be tagged for identification, such as via radio-frequency identification (RFID) tags, barcodes, Quad-codes, and the like. Accordingly, processor 12 may further control access to storage drawers 115 and the containers in them via locking and unlocking an electronic latch closing a lid in storage drawer 115, or in each of the containers therein.

System 100 also includes a centralized pharmacy server 130 having a memory 40, a processor 36, and a communications module 38. Memory 40 includes physician prescribing data 43. Physician data 43 may include a list of physicians and their historical track record of medication prescriptions, associated with one or more patient symptoms and a diagnosis stratified by hospital/health care system care area/geographic area. Memory 40 may include patient data 45, which may be the same as patient data 25, or similar. Patient data 45 may include information associated with patients that receive medications from an automated medication cabinet or a centralized pharmacy. In some embodiments, patient data 45 may include demographic and diagnostic information about the patient (e.g., infant, child, senior, ethnicity and the like), or admission diagnosis. Memory 40 also includes medication data 47. In some embodiments, medication data 47 may further include an inventory list of all medications in the centralized pharmacy, and frequency of prescribing of those medications along with the patients associated with each. Also, memory 40 may further include a predictive algorithm 49.

Predictive algorithm 49 may include instructions which, when executed by processor 36, cause centralize pharmacy server 130 to perform at least partially some steps in methods consistent with the present disclosure. Predictive algorithm 49 may include an intelligence engine that is capable of correlating historical data for medication prescription stratified by hospital service, or care area with patient and physician information and determine prescription patterns. In some embodiments, predictive algorithm 49 may include a neural network algorithm, or a similar non-linear (NN) algorithm configured to provide a prediction of a medication to be delivered to a patient based on the patient admission's data, symptoms, diagnosis, and other information associated with the patient (e.g., demographic data), the patient condition, and the physician or health care professional in charge of the patient. The prescription patterns may be associated to a diagnostic outcome, a seasonal change, or a location within a healthcare facility. Predictive algorithm 49 may be trained over multiple types of input data that a pharmacist operating centralized pharmacy server 130 may find relevant for determining the most optimal combination of medication to stock or have on-hand in a cabinet covering a certain geographic area of the hospital, assuring the maximum percentage of medications are immediately available in the cabinet, based on recent historical prescribing patterns. In some embodiments, predictive algorithm 49 is also configured to account for seasonal changes in medication prescription, disease outbreaks (which may be geographically located), and the like. For example, in some embodiments a seasonal change in medication prescription may include an uptick in antibiotics, vaccines, and other flu-related medication prescriptions during flu season (e.g., during Fall-Winter), an uptick in respiratory decongestant prescriptions during allergy season (e.g., during Spring), and an uptick in skin care prescriptions (e.g., during Summer). More generally, over the course of time the predictive algorithm 49 runs and detects changes in the prescription patterns and recommends changes in the prescription stock for a cabinet based on the predicted changes.

In some embodiments centralized pharmacy server 130 may be coupled with a medication database 160, which may be external to centralized pharmacy server 130, and a computerized physician order entry (CPOE) database 170, also external to centralized pharmacy server 130, according to some embodiments. In some embodiments CPOE database 170 may include prescription patterns aggregated over an extended period of time (e.g., 2-3 years, or maybe more) for different physicians, and for specific patients admitted to a healthcare facility under specific symptoms. In fact, centralized pharmacy center 130 may access CPOE database 170 and use predictive algorithm 49 to correlate a doctor's prescribing practices with the patient's diagnosis and demographic parameters, together with other information to predict medication and doses that will most likely be prescribed to the patient by the doctor. In some embodiments, physicians (e.g., specialist physicians), often admit similar types of patients (e.g., patients showing similar symptoms) to the same specialty areas (e.g., orthopedists admit total hips and total knees to the orthopedic unit, endocrinologists admit type two diabetic patients to the medical unit, and so forth). Prescribing patterns among physicians may be stored in CPOE database 170. Further, in some embodiments CPOE database 170 includes patterns for how physicians admit patients to particular services within a medical center or healthcare facility. Accordingly, predictive algorithm 49 may be configured to identify prescribing patterns, and commonly prescribed medications for each area of a healthcare facility. The predictive algorithm can be used to predictively determine the contents of an automated dispensing machine at the time of initial set-up, based on the stratified physician prescription patterns over some period of time (e.g., weeks or months).

CPOE database 170 includes data accrued over a period of time selected according to a confidence level that the collected data provides statistical significance. For example, CPOE database 170 collects data for a period of time such that averages and other statistical information provides a 5% or 2% of a confidence level.

Automated dispensing machine 110 may be communicatively coupled with centralized pharmacy server 130 through a network 150, via communications module 18 in automated dispensing machine 110 and communications module 38 in centralized pharmacy server 130. Network 150 can include, for example, any one or more of a local area network (LAN), a wide area network (WAN), the Internet, and the like. Further, network 150 can include, but is not limited to, any one or more of the following network topologies, including a bus network, a star network, a ring network, a mesh network, a star-bus network, tree or hierarchical network, and the like. Communications modules 18 and 38 may be configured to couple with network 150 to exchange information between automated dispensing machine 110 and centralized pharmacy center 130. In some embodiments, communications modules 18 and 38 may be configured as a wireless communication hub (e.g., under an IEEE 802.11.xx protocol, an IEEE 802.14.4 protocol, an NFC protocol, a Bluetooth protocol, a BLE protocol, and the like). Memory 20 may include a web-based application having instructions to access centralized pharmacy center 130 and request, retrieve, provide, or update medical information from a patient.

Any one of processors 12 or 36 may include an embedded system micro controller and an operating system configured to execute instructions stored in any one of memories 20 and/or 40.

Figure 2:
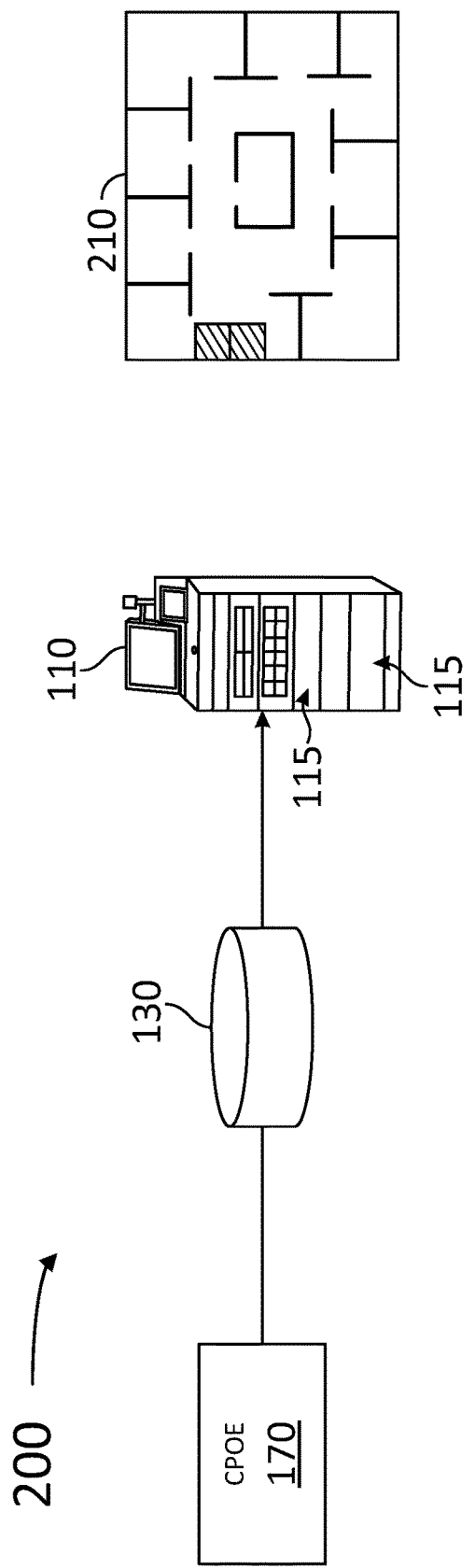
FIG. 2 illustrates a system for medication delivery based on cabinet stockings, patient information, and a cabinet location, according to some embodiments.

FIG. 2 illustrates a system 200 for medication delivery based on cabinet stockings, patient information (e.g., patient data 25 or patient data 45), and a cabinet location 210, according to some embodiments. CPOE 170 may include two to three years of accumulated prescription data associated to physicians and to patient symptoms from a given acute care facility. Accordingly, predictive algorithm 49 may be a neural network trained on CPOE 170 to determine cabinet stocking contents and an optimum location 210 of automated dispensing machine 110. For example, predictive algorithm 49 may determine the contents and location 210 of automated dispensing machine 110 depending on the distribution of patients within the healthcare facility (e.g., room and floor), or even within a single room.

Embodiments consistent with system 200 ensure that the appropriate medication is placed in the vicinity of the patient that most likely will use it within a reasonable amount of time, thereby reducing the time for a caregiver to retrieve the medication when needed. In addition, in some embodiments system 200 is configured to update the contents of automated dispensing machine 110 according to an updated location 210 of automated dispensing machine 110 (e.g., by a wireless locator or GPS attached to automated dispensing machine 110, or simply by updating information logged in the system and transmitted through network 150). Moreover, in some embodiments system 200 is configured to update the desired contents of automated dispensing machine 110 when the patient roster in location 210 is altered (e.g., a new patient is entered and an existing patient is removed, transferred, or checked out).

As a part of the setup or initiation of automated dispensing machine 110 within location 210. System 200 may provide a pharmacist a list, based on the data, of which medications can be removed from the automated dispensing machine, and which medications should be added to cabinet stock, in order to provide the highest probability that any medication prescribed for a patient in the area of the cabinet will be available in the cabinet instead of being delivered from pharmacy 110. For example, in some embodiments predictive algorithm 49 may determine certain medication usage patterns based on common patient diagnosis predicted by the algorithm. To avoid unnecessary storage of such medication, predictive algorithm 49 may indicate to centralized pharmacy server that the given medication at the given location needs to be replaced.

Figure 3:
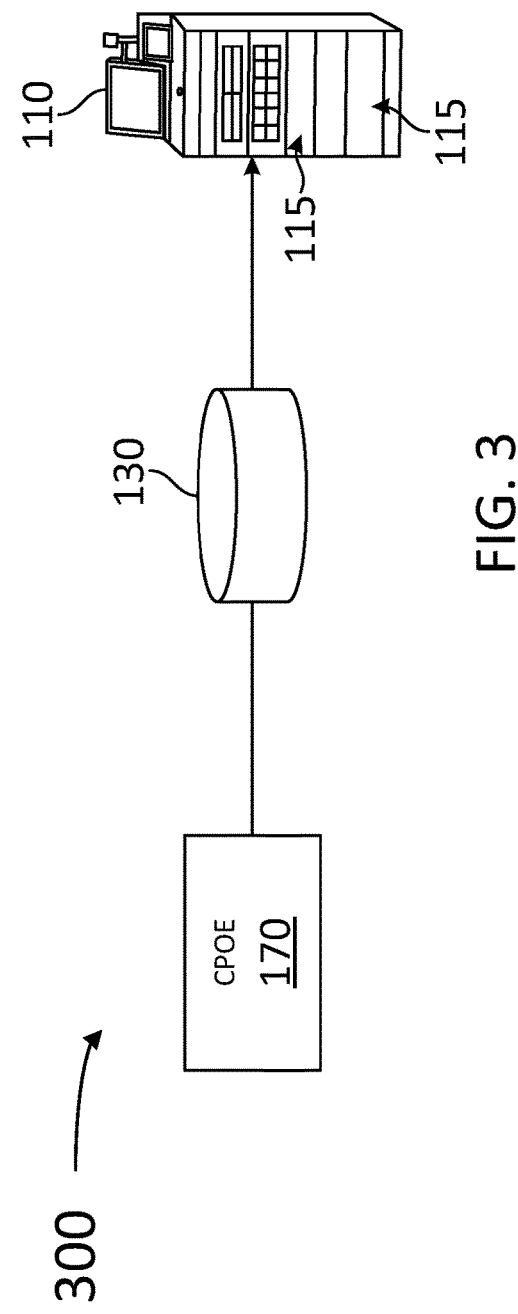
FIG. 3 illustrates a system for medication delivery based on cabinet stockings, patient information, and a storage optimization, according to some embodiments.

FIG. 3 illustrates a system 300 for medication delivery based on cabinet stockings, patient information, and a storage optimization including an auto-optimization tool, according to some embodiments. Based on CPOE database 170, system 300 processes predictive algorithm 49 in centralized pharmacy database 130 to adjust and align the inventory in automated dispensing machine 110 with a current physician prescription. Predictive algorithm 49 analyzes prescription data from CPOE database stratified by hospital care area 170 to determine contents of automated dispensing machine 110 that may be removed and replaced with more frequently used medications. In some embodiments, system 300 updates and adjusts the contents of automated dispensing machine 110 on a routine basis. Thus, system 300 may substantially reduce extra costs currently experienced for medication management in healthcare facilities. For example, in some embodiments as high as 20% of medications stocked in the cabinet may not be among the current commonly prescribed medications, requiring them to be delivered from pharmacy may be on a one-off basis at a much higher cost.

Figure 4:
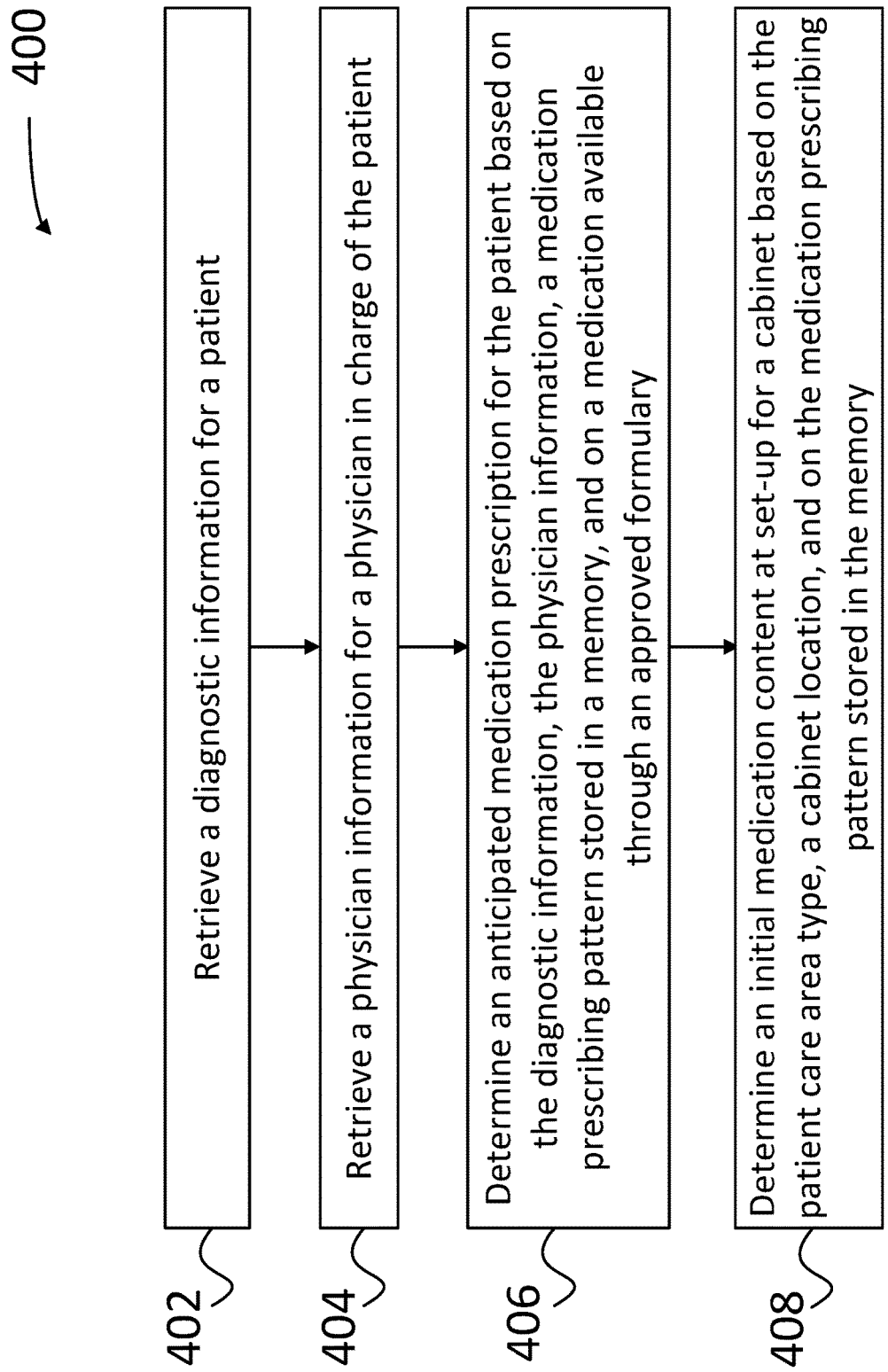
FIG. 4 is a flow chart illustrating steps in a method for predictive medication prescription, according to some embodiments.

FIG. 4 is a flow chart illustrating steps in a method 400 for predictive medication prescription, according to some embodiments. At least some of the steps in method 400 may be performed by a computer having a processor executing commands stored in a memory of the computer (e.g., automated dispensing machine 110, centralized pharmacy server 130, processors 12, or 36, and memories 20 or 40). At least some of the steps in method 400 may be performed by an automated dispensing machine, including one or more storage drawers, each storage drawer having at least one or more containers, the containers including medications or any other tagged items (e.g., automated dispensing machine 110, and storage drawers 115). In some embodiments, steps in method 400 may be partially performed by an automated dispensing machine and by a centralized pharmacy server being communicatively coupled with one another via communication modules, through a network (e.g., communications modules 18 and 38, and network 150). Further, steps as disclosed in method 400 may include retrieving, editing, and/or storing files in a database that is part of, or is communicably coupled to, the computer (e.g., medication database 160 or CPOE database 170). Methods consistent with the present disclosure may include at least some, but not all of the steps illustrated in method 400, performed in a different sequence. Furthermore, methods consistent with the present disclosure may include at least two or more steps as in method 400, performed overlapping in time, or almost simultaneously.

Step 402 includes retrieving a diagnostic information for a patient. In some embodiments, step 402 includes retrieving a demographic data for the patient.

Step 404 includes retrieving a physician information for a physician in charge of the patient. The physician information may include one or more areas of specialty of the physician, and a prescription history for the physician. In some embodiments, step 404 may include retrieving a physician information including a prescribing pattern over a length of time for a selected area of a healthcare facility where the automated dispensing machine is located.

Step 406 includes determining an anticipated medication prescription for the patient based on the diagnostic information, the physician information, a medication prescribing pattern stored in the memory, and on a medication available through an approved formulary. In some embodiments, step 406 includes retrieving a location information for the patient relative to a location information for the automated dispensing machine configured to store the medication, to determine the medication to be prescribed. In some embodiments, the medication prescribing pattern stored in the memory includes a prescribing pattern of multiple physicians in a selected area (e.g., where the patient or the automated dispensing machine are located). In some embodiments, step 406 includes determining the medication to be prescribed based on a change of the pre-determined pattern stored in the memory. Further, in some embodiments step 406 includes a history of medication prescriptions of the physician for determining the medication to be prescribed. In some embodiments, the pre-determined pattern stored in the memory comprises a seasonal change of a medication prescription, and a prescription data stored for an extended period of time in the memory.

In some embodiments, step 406 further includes unlocking a storage drawer in an automated dispensing machine for providing to a healthcare professional access to the medication, or for preplacement of the anticipated medication prescription. In some embodiments, step 406 includes locking the storage drawer until a professional healthcare provider places an order including the anticipated medication prescription. In some embodiments, step 406 further includes storing the medication in the automated dispensing machine based on a location of the automated dispensing machine. In some embodiments, step 406 includes requesting a replacement of the medication in a storage drawer of an automated dispensing machine where the medication is stored.

Step 408 includes determining the initial medication cabinet contents at set-up based on the patient care area type, location and on the medication prescribing pattern stored in the memory. Accordingly, step 408 may include identifying (e.g., by a pharmacist or a central computer in the pharmacy) prescribing patterns among physicians and patterns in how those physicians admit patients to particular services within a medical center (e.g., what patients are assigned to which locations). Step 408 may include identifying medication prescribing patterns and commonly prescribed medications for each area of a facility. In some embodiments, step 408 may include determining the initial number, size, location, and contents at set-up for each of multiple cabinets arranged in a facility based on the patient care area type, location, and on a medication prescribing pattern.

Figure 5:
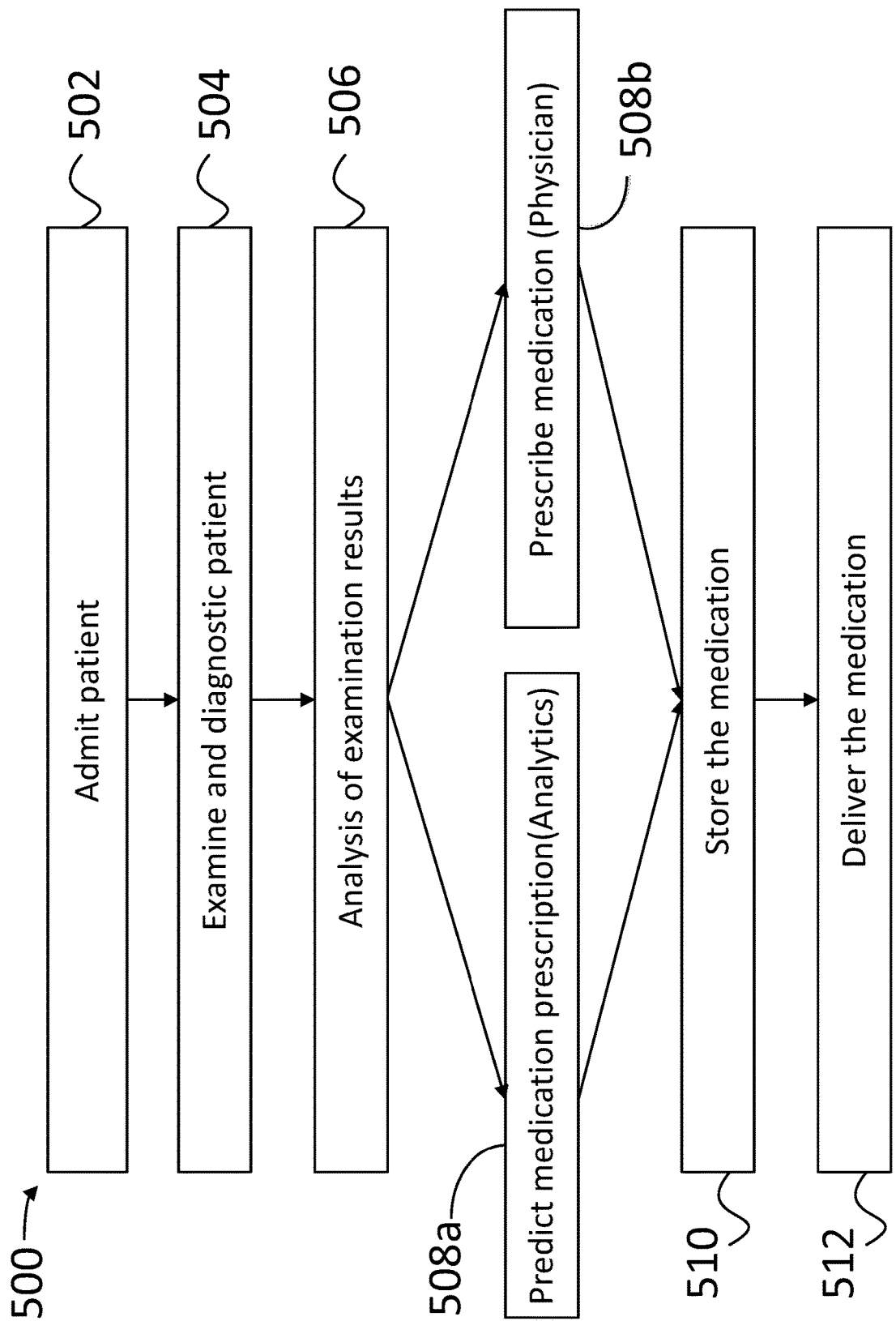
FIG. 5 is a flow chart illustrating steps in a method for predictive medication management, according to some embodiments.

FIG. 5 is a flow chart illustrating steps in a method 500 for predictive medication management, according to some embodiments. At least some of the steps in method 500 may be performed by a computer having a processor executing commands stored in a memory of the computer (e.g., automated dispensing machine 110, centralized pharmacy server 130, processors 12, or 36, and memories 20 or 40). At least some of the steps in method 500 may be performed by an automated dispensing machine, including one or more storage drawers, each storage drawer having at least one or more containers, the containers including medications or any other tagged items (e.g., automated dispensing machine 110, and storage drawers 115). In some embodiments, steps in method 500 may be partially performed by an automated dispensing machine and by a centralized pharmacy server being communicatively coupled with one another via communication modules, through a network (e.g., communications modules 18 and 38, and network 150). Further, steps as disclosed in method 500 may include retrieving, editing, and/or storing files in a database that is part of, or is communicably coupled to, the computer (e.g., medication database 160 or CPOE database 170). Methods consistent with the present disclosure may include at least some, but not all of the steps illustrated in method 500, performed in a different sequence. Furthermore, methods consistent with the present disclosure may include at least two or more steps as in method 500, performed overlapping in time, or almost simultaneously.

Step 502 includes admitting a patient to a healthcare facility. In some embodiments, step 502 includes collecting and storing relevant patient data in the memory. The relevant patient data may include personal patient information, such as demographic data (e.g., age, gender, and the like), and also symptoms suffered by the patient.

Step 504 includes examining and diagnosing the patient based on the relevant patient data.

Step 506 includes analyzing the examination results based on clinical protocols.

Step 508a includes predicting the medication prescription using analytics methods as disclosed herein. In some embodiments, step 508a includes anticipating the desire for a medication and placing the medication in a location near the patient prior to, or even simultaneously with, the physician prescribing the medication to the patient. In some embodiments, step 508a includes retrieving the personal information from the patient upon admission of the patient to a healthcare facility (e.g., step 502), the personal information comprising a symptom. Further, in some embodiments step 508a includes retrieving a diagnostic based on the symptom (e.g., step 504). Moreover, in some embodiments step 508a includes determining a predicted medication prescription for the patient based on the personal information for the patient, on the diagnostic, and on a pre-determined prescription pattern stored in a memory (e.g., from CPOE database 170).

Step 508b includes prescribing a selected medication by the physician.

Step 510 includes storing the medication. In some embodiments, step 510 includes locking a storage drawer in the automated dispensing machine by actuating an electronic latch for a lid in the storage drawer.

Step 512 includes delivering, by a nurse or other healthcare professional, the selected prescription medication to a patient. In some embodiments, step 512 includes unlocking a storage drawer in the automated dispensing machine by actuating an electronic latch for a lid in the storage drawer.

Figure 6:
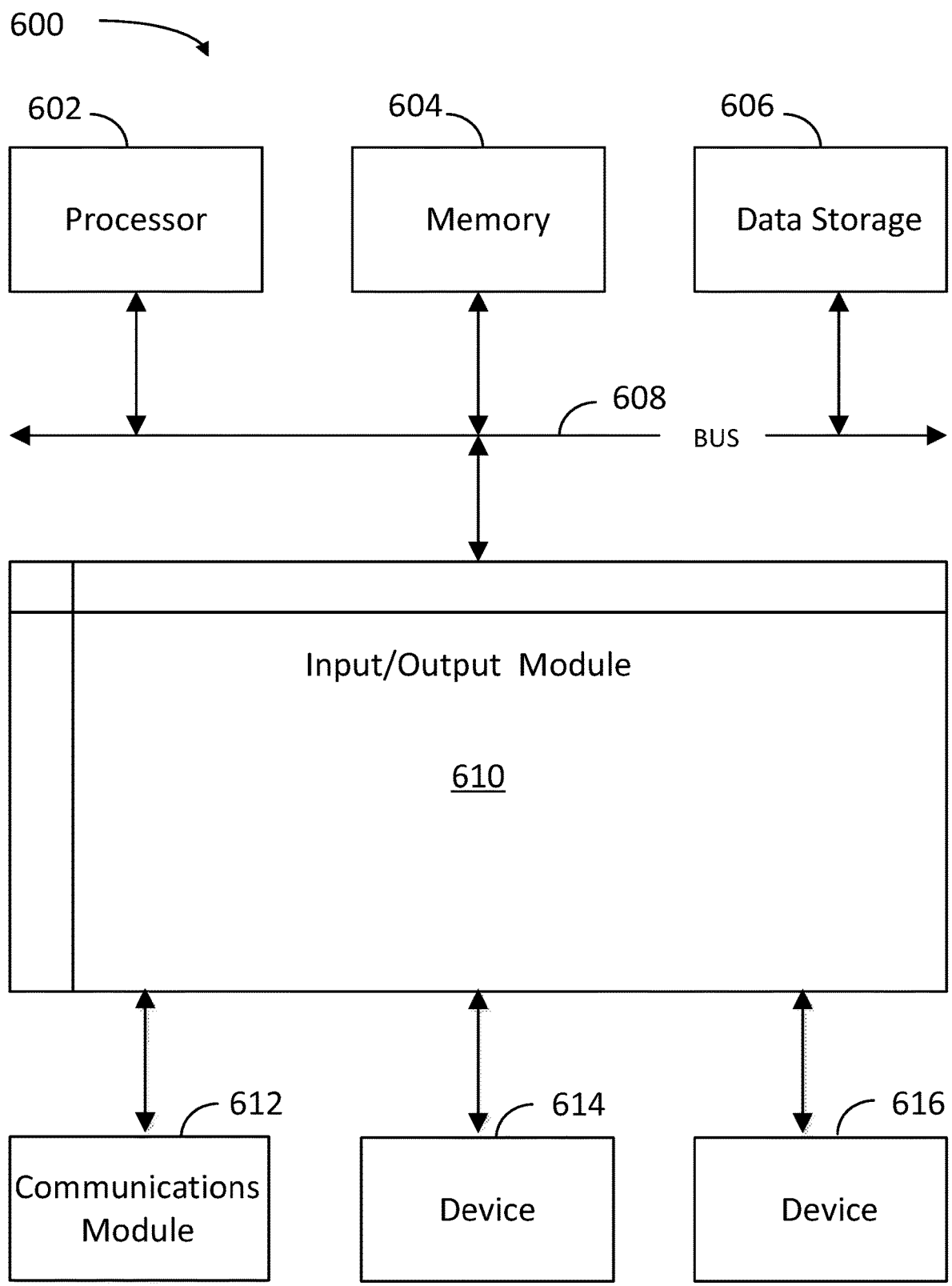
FIG. 6 is a block diagram illustrating an example computer system with which the methods and steps can be implemented, according to some embodiments.

FIG. 6 is a block diagram illustrating an example computer system 500 with which the methods and steps illustrated in methods 400 and 500 can be implemented, according to some embodiments. In certain aspects, computer system 600 can be implemented using hardware or a combination of software and hardware, either in a dedicated server, integrated into another entity, or distributed across multiple entities.

Computer system 600 includes a bus 608 or other communication mechanism for communicating information, and a processor 602 coupled with bus 608 for processing information. By way of example, computer system 600 can be implemented with one or more processors 602. Processor 602 can be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable entity that can perform calculations or other manipulations of information. In some embodiments, processor 602 may include modules and circuits configured as a 'placing' tool or engine, or a 'routing' tool or engine, to place devices and route channels in a circuit layout, respectively and as disclosed herein.

Computer system 600 includes, in addition to hardware, code that creates an execution environment for the computer program in question, e.g., code that constitutes processor firmware, a protocol stack, a database management system, an operating system, or a combination of one or more of them stored in an included memory 604, such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, or any other suitable storage device, coupled to bus 608 for storing information and instructions to be executed by processor 602. Processor 602 and memory 604 can be supplemented by, or incorporated in, special purpose logic circuitry.

The instructions may be stored in memory 604 and implemented in one or more computer program products, e.g., one or more modules of computer program instructions encoded on a computer readable medium for execution by, or to control the operation of, the computer system 600, and according to any method well known to those of skill in the art, including, but not limited to, computer languages such as data-oriented languages (e.g., SQL, dBase), system languages (e.g., C, Objective-C, C++, Assembly), architectural languages (e.g., Java, .NET), and application languages (e.g., PHP, Ruby, Perl, Python). Instructions may also be implemented in computer languages such as array languages, aspect-oriented languages, assembly languages, authoring languages, command line interface languages, compiled languages, concurrent languages, curly-bracket languages, dataflow languages, data-structured languages, declarative languages, esoteric languages, extension languages, fourth-generation languages, functional languages, interactive mode languages, interpreted languages, iterative languages, list-based languages, little languages, logic-based languages, machine languages, macro languages, metaprogramming languages, multiparadigm languages, numerical analysis, non-English-based languages, object-oriented class-based languages, object-oriented prototype-based languages, off-side rule languages, procedural languages, reflective languages, rule-based languages, scripting languages, stack-based languages, synchronous languages, syntax handling languages, visual languages, Wirth languages, embeddable languages, and xml-based languages. Memory 604 may also be used for storing temporary variable or other intermediate information during execution of instructions to be executed by processor 602.

A computer program as discussed herein does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network. The processes and logic flows described in this specification can be performed by one or more programmable processors executing one or more computer programs to perform functions by operating on input data and generating output.

Computer system 600 further includes a data storage device 606 such as a magnetic disk or optical disk, coupled to bus 608 for storing information and instructions.

Computer system 600 is coupled via input/output module 610 to various devices. The input/output module 610 is any input/output module. Example input/output modules 610 include data ports such as USB ports. The input/output module 610 is configured to connect to a communications module 612. Example communications modules 612 include networking interface cards, such as Ethernet cards and modems. In certain aspects, the input/output module 610 is configured to connect to a plurality of devices, such as an input device 614 and/or an output device 616. Example input devices 614 include a keyboard and a pointing device, e.g., a mouse or a trackball, by which a user can provide input to the computer system 600. Other kinds of input devices 614 are used to provide for interaction with a user as well, such as a tactile input device, visual input device, audio input device, or brain-computer interface device. For example, feedback provided to the user can be any form of sensory feedback, e.g., visual feedback, auditory feedback, or tactile feedback; and input from the user can be received in any form, including acoustic, speech, tactile, or brain wave input. Example output devices 616 include display devices, such as a LED (light emitting diode), CRT (cathode ray tube), or LCD (liquid crystal display) screen, for displaying information to the user.

Methods as disclosed herein may be performed by computer system 600 in response to processor 602 executing one or more sequences of one or more instructions contained in memory 604. Such instructions may be read into memory 604 from another machine-readable medium, such as data storage device 606. Execution of the sequences of instructions contained in main memory 604 causes processor 602 to perform the process steps described herein (e.g., as in methods 400 and 500). One or more processors in a multi-processing arrangement may also be employed to execute the sequences of instructions contained in memory 604. In alternative aspects, hard-wired circuitry may be used in place of or in combination with software instructions to implement various aspects of the present disclosure. Thus, aspects of the present disclosure are not limited to any specific combination of hardware circuitry and software.

Various aspects of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. The communication network can include, for example, any one or more of a personal area network (PAN), a local area network (LAN), a campus area network (CAN), a metropolitan area network (MAN), a wide area network (WAN), a broadband network (BBN), the Internet, and the like. Further, the communication network can include, but is not limited to, for example, any one or more of the following network topologies, including a bus network, a star network, a ring network, a mesh network, a star-bus network, tree or hierarchical network, or the like. The communications modules can be, for example, modems or Ethernet cards.

Computing system 600 includes servers and personal computer devices. A personal computing device and server are generally remote from each other and typically interact through a communication network. The relationship of client and server arises by virtue of computer programs running on the respective computers and having a client-server relationship to each other. Computer system 600 can be, for example, and without limitation, a desktop computer, laptop computer, or tablet computer. Computer system 600 can also be embedded in another device, for example, and without limitation, a mobile telephone, a personal digital assistant (PDA), a mobile audio player, a Global Positioning System (GPS) receiver, a video game console, and/or a television set top box.

The term "machine-readable storage medium" or "computer readable medium" as used herein refers to any medium or media that participates in providing instructions or data to processor 602 for execution. Such a medium may take many forms, including, but not limited to, non-volatile media, volatile media, and transmission media. Non-volatile media include, for example, optical disks, magnetic disks, or flash memory, such as data storage device 606. Volatile media include dynamic memory, such as memory 604. Transmission media include coaxial cables, copper wire, and fiber optics, including the wires that comprise bus 608. Common forms of machine-readable media include, for example, floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH EPROM, any other memory chip or cartridge, or any other medium from which a computer can read. The machine-readable storage medium can be a machine-readable storage device, a machine-readable storage substrate, a memory device, a composition of matter effecting a machine-readable propagated signal, or a combination of one or more of them.

In one aspect, a method may be an operation, an instruction, or a function and vice versa. In one aspect, a clause or a claim may be amended to include some or all of the words (e.g., instructions, operations, functions, or components) recited in other one or more clauses, one or more words, one or more sentences, one or more phrases, one or more paragraphs, and/or one or more claims.

To illustrate the interchangeability of hardware and software, items such as the various illustrative blocks, modules, components, methods, operations, instructions, and algorithms have been described generally in terms of their functionality. Whether such functionality is implemented as hardware, software or a combination of hardware and software depends upon the particular application and design constraints imposed on the overall system. Skilled artisans may implement the described functionality in varying ways for each particular application.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

As used herein, the phrase "at least one of" preceding a series of items, with the term "and" or "or" to separate any of the items, modifies the list as a whole, rather than each member of the list (e.g., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Furthermore, to the extent that the term "include," "have," or the like is used in the description or the claims, such term is intended to be inclusive in a manner similar to the term "comprise" as "comprise" is interpreted when employed as a transitional word in a claim. The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." The term "some" refers to one or more. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

What is claimed is:

1. A system, comprising:
    a locator device associated with an automated dispensing machine;
    a memory storing instructions; and
    a processor configured to execute the instructions to:
        determine a patient roster of a healthcare facility has been updated;
        after detecting the patient roster was updated:
            determine a current device location of the locator device;
            determine a patient location of a patient relative to the current device location;
            retrieve a diagnostic information for the patient;
            identify at least one prescribing pattern of one or more physicians, one of the physicians having a prescribing relationship with the patient;
            provide the current device location, the patient location, the diagnostic information for the patient, and the at least one prescribing pattern to a predictive algorithm;
            determine an inventory update for the automated dispensing machine based on providing the current device location and the patient location, the diagnostic information, and the at least one prescribing pattern to the predictive algorithm;
            cause, responsive to determining the inventory update, an adjustment to a current inventory of the automated dispensing machine based on the current inventory and the inventory update, and
            cause, in connection with causing the adjustment or a delivery of a respective medication stored in the automated dispensing machine, actuation of an electronic latch associated with a storage location within the automated dispensing machine.

2. The system of claim 1, wherein the storage location comprises a storage drawer, and wherein the processor is further configured to lock the storage drawer until a medication associated with the inventory update is prescribed and delivered by a professional healthcare provider.

3. The system of claim 1, wherein the processor is further configured to:
    cause delivery of a first dose and subsequent supply of a medication; and
    cause storage of the first dose and subsequent supply of the medication in the automated dispensing machine.

4. The system of claim 1, wherein the processor is configured to determine an anticipated medication prescription for the patient based on providing to the predictive algorithm the current device location and the patient location, the diagnostic information, and historical medication prescribing patterns associated with an area corresponding to the current device location or the patient location.

5. The system of claim 4, wherein the area of the healthcare facility comprises an acute care area.

6. The system of claim 4, wherein the historical medication prescribing patterns are stored in the memory, and processor is further configured to determine the inventory update based on a change of a medication prescribing pattern of the historical medication prescribing patterns stored in the memory.

7. The system of claim 4, wherein the historical medication prescribing patterns are stored in the memory and comprise a history of medication prescriptions of one or more physicians associated with patients having similar diagnosis to the patient.

8. The system of claim 4, wherein the historical medication prescribing patterns are stored in the memory and comprise a trend and a change in a medication prescription pattern over a period of time.

9. The system of claim 4, wherein the historical medication prescribing patterns are stored in the memory and comprise a prescription data stored for an extended a period of time greater than a week in the memory.

10. The system of claim 1, further comprising the automated dispensing machine, wherein the processor is configured to determine the respective medication is available through a formulary for the healthcare facility.

11. A computer-implemented method, comprising:
    determining a patient roster of a healthcare facility has been updated;
    after determining the patient roster was updated:
        determining a current device location of a locator device attached to an automated dispensing machine;
        determining a current device location of the locator device;
        determining a patient location of a patient relative to the current device location;
        obtaining a diagnostic information for the patient;
        identifying at least one prescribing pattern of one or more physicians, one of the physicians having a prescribing relationship with the patient;

providing the current device location, the patient location, the diagnostic information for the patient, and the at least one prescribing pattern to a predictive algorithm;

determining an inventory update for the automated dispensing machine based on providing the current device location and the patient location, the diagnostic information, and the at least one prescribing pattern to the predictive algorithm;

causing, responsive to determining the inventory update, an adjustment to a current inventory of the automated dispensing machine based on the current inventory and the inventory update, and causing, in connection with causing the adjustment or a delivery of a respective medication stored in the automated dispensing machine, actuation of an electronic latch associated with a storage location within the automated dispensing machine.

12. The computer-implemented method of claim 11, wherein the storage location comprises a storage drawer, and wherein the method further comprises:

locking the storage drawer until a medication associated with the inventory update is prescribed and delivered by a professional healthcare provider.

13. The computer-implemented method of claim 11, the method further comprising:

causing delivery of a first dose and subsequent supply of a medication; and causing storage of the first dose and subsequent supply of the medication in the automated dispensing machine.

14. The computer-implemented method of claim 11, wherein the method further comprises:

determining an anticipated medication prescription for the patient based on providing to the predictive algorithm the current device location and the patient location, the diagnostic information, and historical medication prescribing patterns associated with an area corresponding to the current device location or the patient location.

15. The computer-implemented method of claim 14, wherein the area of the healthcare facility comprises an acute care area.

16. The computer-implemented method of claim 14, wherein the historical medication prescribing patterns are stored in a non-transitory computer readable memory, and processor is further configured to determine the inventory update based on a change of a medication prescribing pattern of the historical medication prescribing patterns stored in the memory; or wherein the historical medication prescribing patterns are stored in the memory and comprise a history of medication prescriptions of one or more physicians associated with patients having similar diagnosis to the patient; or wherein the medication prescribing patterns are stored in the memory and comprise a trend and a change in a medication prescription pattern over a period of time; or wherein the medication prescribing patterns are stored in the memory and comprise a prescription data stored for an extended a period of time greater than a week in the memory.

17. The computer-implemented method of claim 11, the method further comprising:

determining the respective medication is available through a formulary for the healthcare facility.

18. The computer-implemented method of claim 11, wherein determining the patient roster of the healthcare facility has been updated comprises determining that the patient was admitted to, removed from, transferred within, or checked out of the healthcare facility.

19. A non-transitory, computer readable medium comprising instructions which, when executed by a computing device, cause the computing device to perform operations, comprising:

determining a patient roster of a healthcare facility has been updated;

after determining the patient roster was updated:

determining a current device location of a locator device attached to an automated dispensing machine;

determining a current device location of the locator device;

determining a patient location of a patient relative to the current device location;

obtaining a diagnostic information for the patient;

identifying at least one prescribing pattern of one or more physicians, one of the physicians having a prescribing relationship with the patient;

providing the current device location, the patient location, the diagnostic information for the patient, and the at least one prescribing pattern to a predictive algorithm;

determining an inventory update for the automated dispensing machine based on providing the current device location and the patient location, the diagnostic information, and the at least one prescribing pattern to the predictive algorithm;

causing, responsive to determining the inventory update, an adjustment to a current inventory of the automated dispensing machine based on the current inventory and the inventory update, and causing, in connection with causing the adjustment or a delivery of a respective medication stored in the automated dispensing machine, actuation of an electronic latch associated with a storage location within the automated dispensing machine.

20. The non-transitory, computer-readable medium of claim 19, wherein the operations further comprise:

determining an anticipated medication prescription for the patient based on providing to the predictive algorithm the current device location and the patient location, the diagnostic information, and historical medication prescribing patterns associated with an area corresponding to the current device location or the patient location.

* * * * *